United States Patent
Shiba et al.

(10) Patent No.: US 12,232,813 B2
(45) Date of Patent: Feb. 25, 2025

(54) OPHTHALMIC IMAGE PROCESSING DEVICE, OPHTHALMIC IMAGE PROCESSING PROGRAM, AND OPHTHALMIC IMAGE PROCESSING SYSTEM

(71) Applicant: NIDEK CO., LTD., Gamagori (JP)

(72) Inventors: Ryosuke Shiba, Gamagori (JP); Sohei Miyazaki, Gamagori (JP); Yoshiki Kumagai, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 651 days.

(21) Appl. No.: 17/614,428

(22) PCT Filed: May 28, 2020

(86) PCT No.: PCT/JP2020/021231
§ 371 (c)(1),
(2) Date: Nov. 26, 2021

(87) PCT Pub. No.: WO2020/241794
PCT Pub. Date: Dec. 3, 2020

(65) Prior Publication Data
US 2022/0225877 A1    Jul. 21, 2022

(30) Foreign Application Priority Data
May 31, 2019  (JP) .................................. 2019-102913

(51) Int. Cl.
*A61B 3/14* (2006.01)
*A61B 3/10* (2006.01)
(Continued)

(52) U.S. Cl.
CPC ................ *A61B 3/14* (2013.01); *A61B 3/102* (2013.01); *A61B 5/7264* (2013.01); *G06T 7/0012* (2013.01); *G06T 2207/30041* (2013.01)

(58) Field of Classification Search
CPC ......... A61B 3/14; A61B 3/102; A61B 5/7264; G06T 7/0012; G06T 2207/30041;
(Continued)

(56) References Cited

U.S. PATENT DOCUMENTS

2011/0134393 A1   6/2011 Iwase
2011/0242306 A1 * 10/2011 Bressler ............... A61B 3/0025
                                                  382/128
(Continued)

FOREIGN PATENT DOCUMENTS

| EP | 2638848 B1 * | 3/2019 | ............. A61B 3/102 |
|----|----|----|----|
| JP | 2011-120657 A | 6/2011 | |
| JP | 2014-104275 A | 6/2014 | |
| JP | 2018-005841 A | 1/2018 | |

OTHER PUBLICATIONS

Jul. 14, 2020 International Search Report issued in International Patent Application No. PCT/JP2020/021231.
(Continued)

*Primary Examiner* — Tuyen Tra
*Assistant Examiner* — Rahman Abdur
(74) *Attorney, Agent, or Firm* — Oliff PLC

(57) ABSTRACT

A control section of an ophthalmologic image processing apparatus acquires an ophthalmologic image captured by an ophthalmologic image capturing apparatus. The control section acquires, for the acquired ophthalmologic image, evaluation information indicating an appropriateness for acquiring medical data including at least any of an analysis result relating to a disease of a subject eye, an analysis result relating to the structure of the subject eye, and an image converted from the acquired ophthalmologic image. The control section acquires the medical data based on the acquired ophthalmologic image. The control section changes a medical data acquisition method according to
(Continued)

whether or not the evaluation information on the ophthalmologic image satisfies a criterion.

10 Claims, 7 Drawing Sheets

(51) Int. Cl.
*A61B 5/00* (2006.01)
*G06T 7/00* (2017.01)

(58) Field of Classification Search
CPC . G06T 2207/10101; G06T 2207/20081; G06T 2207/20084; G06T 2207/30168
USPC ........................................................ 351/206
See application file for complete search history.

(56) References Cited

U.S. PATENT DOCUMENTS

| | | | |
|---|---|---|---|
| 2012/0230564 A1* | 9/2012 | Liu ...................... | A61B 3/0025 382/128 |
| 2016/0198939 A1* | 7/2016 | Fukuhara ............. | A61B 3/1225 351/246 |
| 2018/0315193 A1* | 11/2018 | Paschalakis .............. | G06T 7/11 |

OTHER PUBLICATIONS

Yufan He, Aaron Carass, et al. "Topology guaranteed segmentation of the human retina from OCT using convolutional neural networks." arXiv: 1803. 05120, Mar. 14, 2018.

\* cited by examiner

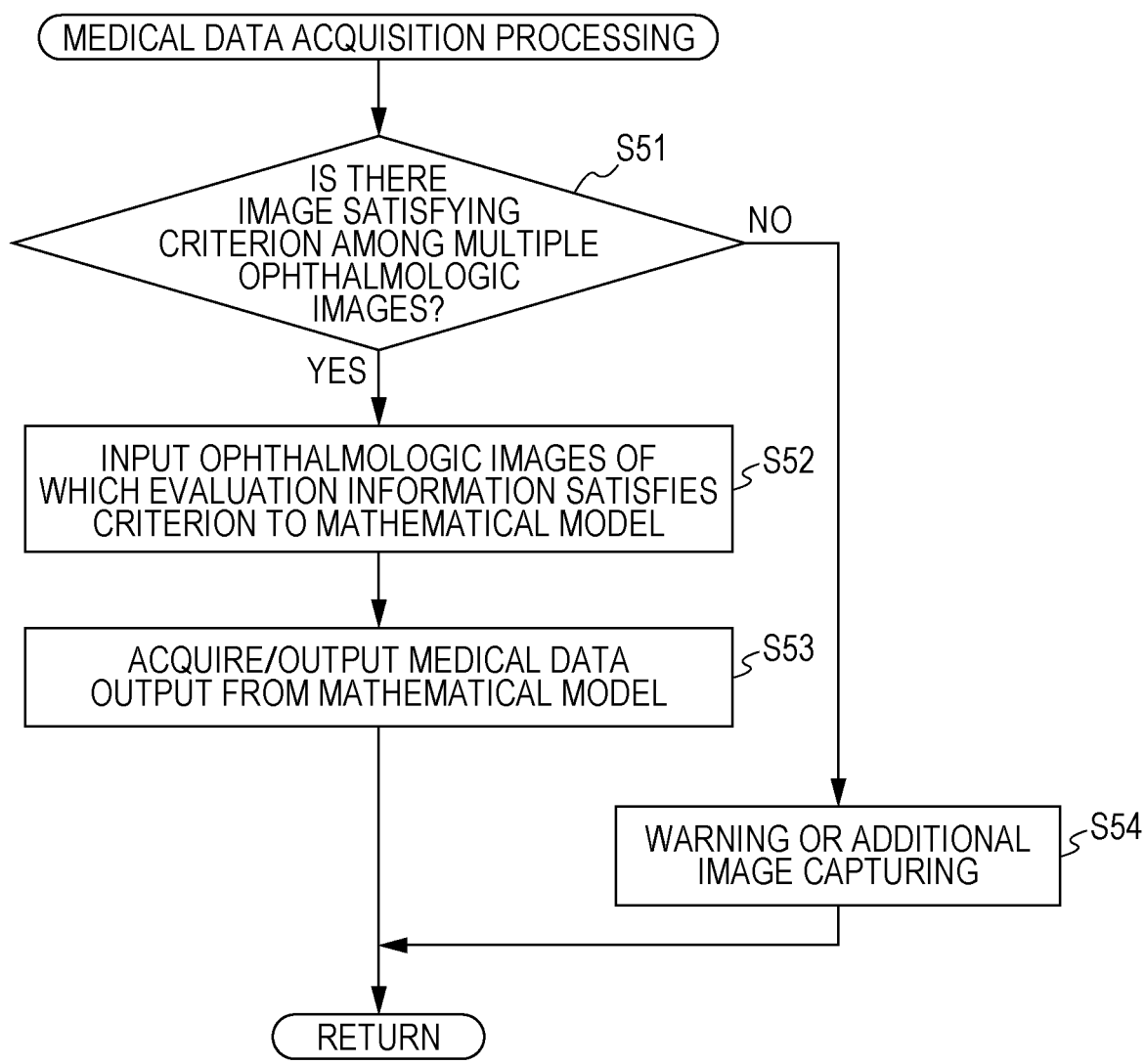

OPHTHALMIC IMAGE PROCESSING DEVICE, OPHTHALMIC IMAGE PROCESSING PROGRAM, AND OPHTHALMIC IMAGE PROCESSING SYSTEM

TECHNICAL FIELD

The present disclosure relates to an ophthalmologic image processing apparatus, an ophthalmologic image processing program, and an ophthalmologic image processing system used for processing an ophthalmologic image of a subject eye.

BACKGROUND ART

In recent years, the technique of acquiring various types of medical data based on an ophthalmologic image of a subject eye has been proposed. For example, in a technique disclosed in Non-Patent Literature 1, an analysis result relating to a boundary of each layer of a tissue shown on an ophthalmologic image is acquired based on the ophthalmologic image. Moreover, it is conceivable that an analysis result relating to a disease of a subject eye or an image converted from the ophthalmologic image is acquired based on the captured ophthalmologic image.

CITATION LIST

Non-Patent Literature

NON-PATENT LITERATURE 1: Yufan He, Aaron Carass, et al. "Topology guaranteed segmentation of the human retina from OCT using convolutional neural networks." arXiv:1803.05120, 14 Mar. 2018

SUMMARY OF INVENTION

In a case where medical data is acquired based on an ophthalmologic image, the captured ophthalmologic image might be an ophthalmologic image not suitable for acquiring the medical data in some cases. If the medical data is acquired based on the improper ophthalmologic image, the reliability of the medical data is degraded, and in many cases, data useful for doctors or the like cannot be obtained.

A typical object of the present disclosure is to provide an ophthalmologic image processing apparatus, an ophthalmologic image processing program, and an ophthalmologic image processing system capable of properly acquiring medical data based on an ophthalmologic image.

An ophthalmologic image processing apparatus provided by a typical embodiment of the present disclosure is for processing an ophthalmologic image as an image of a tissue of a subject eye, in which a control section of the ophthalmologic image processing apparatus executing: an image acquisition step of acquiring an ophthalmologic image captured by an ophthalmologic image capturing apparatus; an evaluation information acquisition step of acquiring, for the ophthalmologic image acquired at the image acquisition step, evaluation information indicating an appropriateness for acquiring medical data including at least any of an analysis result relating to a disease of the subject eye, an analysis result relating to a structure of the subject eye, and an image converted from the acquired ophthalmologic image; and a medical data acquisition step of acquiring the medical data based on the ophthalmologic image acquired at the image acquisition step, and at the medical data acquisition step, the control section changing a medical data acquisition method according to whether or not the evaluation information acquired at the evaluation information acquisition step satisfies a criterion.

An ophthalmologic image processing program provided by a typical embodiment of the present disclosure is executed by an ophthalmologic image processing apparatus for processing an ophthalmologic image as an image of a tissue of a subject eye. Execution of the ophthalmologic image processing program by a control section of the ophthalmologic image processing apparatus causes the ophthalmologic image processing apparatus to execute: an image acquisition step of acquiring an ophthalmologic image captured by an ophthalmologic image capturing apparatus; an evaluation information acquisition step of acquiring, for the ophthalmologic image acquired at the image acquisition step, evaluation information indicating an appropriateness for acquiring medical data including at least any of an analysis result relating to a disease of the subject eye, an analysis result relating to a structure of the subject eye, and an image converted from the acquired ophthalmologic image; and a medical data acquisition step of acquiring the medical data based on the ophthalmologic image acquired at the image acquisition step, and at the medical data acquisition step, a medical data acquisition method being changed according to whether or not the evaluation information acquired at the evaluation information acquisition step satisfies a criterion.

An ophthalmologic image processing system provided by a typical embodiment of the present disclosure is for processing an ophthalmologic image as an image of a tissue of a subject eye. The ophthalmologic image processing system includes an OCT apparatus configured to receive interfering light of reference light and reflected light of measurement light emitted to the tissue of the subject eye to capture an ophthalmologic image as a laminagram image of the tissue. A control section of the ophthalmologic image processing system executes: an image acquisition step of acquiring an ophthalmologic image captured by the OCT apparatus; an evaluation information acquisition step of acquiring, for the ophthalmologic image acquired at the image acquisition step, evaluation information indicating an appropriateness for acquiring medical data including at least any of an analysis result relating to a disease of the subject eye, an analysis result relating to a structure of the subject eye, and an image converted from the acquired ophthalmologic image; an addition step of executing, in a case where the evaluation information acquired at the evaluation information acquisition step does not satisfy a criterion, processing of additionally capturing an image of a location identical to that of the ophthalmologic image and addition averaging processing of the image captured in addition to the ophthalmologic image; and a medical data acquisition step of acquiring the medical data in such a manner that the ophthalmologic image subjected to the addition averaging processing is input to a mathematical model trained according to a machine learning algorithm.

According to the ophthalmologic image processing apparatus, the ophthalmologic image processing program, and the ophthalmologic image processing system of the present disclosure, the medical data can be properly acquired based on the ophthalmologic image.

The control section of the ophthalmologic image processing apparatus described as an example in the present disclosure executes the image acquisition step, the evaluation information acquisition step, and the medical data acquisition step. At the image acquisition step, the control section acquires the ophthalmologic image captured by the ophthalmologic image capturing apparatus. At the evaluation information acquisition step, the control section acquires, for the ophthalmologic image acquired at the image acquisition step, the evaluation information indicating the appropriateness for acquiring the medical data. The medical data is at least any data of the analysis result relating to the disease of the subject eye, the analysis result relating to the structure of the subject eye, and the image converted from the ophthalmologic image. At the medical data acquisition step, the control section acquires the medical data based on the ophthalmologic image acquired at the image acquisition step. At the medical data acquisition step, the control section changes the medical data acquisition method according to whether or not the evaluation information on the ophthalmologic image satisfies the criterion.

According to the ophthalmologic image processing apparatus described as the example in the present disclosure, the evaluation information indicating the appropriateness for acquiring the medical data is acquired for the ophthalmologic image, and the medical data acquisition method is changed according to the evaluation information. Thus, the medical data is properly acquired from the ophthalmologic image according to the evaluation information on the ophthalmologic image.

Note that various parameters relating to the quality of the ophthalmologic image can be used as necessary as the evaluation information on the ophthalmologic image. For example, an index (e.g., a signal strength index (SSI) or a quality index (QI)) indicating the strength of the signal of the ophthalmologic image or the goodness of the signal may be used as the evaluation information on the ophthalmologic image. Alternatively, at least any of the ratio (a signal to noise ratio (SNR) of a noise level to an image signal level, a background noise level, an image contrast or the like may be used as the evaluation information on the ophthalmologic image. Alternatively, an image capturing condition (e.g., at least any of a condition relating to scanning, an exposure time or the like when the ophthalmologic image is captured by scanning of the tissue with light) when the ophthalmologic image is captured by the ophthalmologic image capturing apparatus may be used as the evaluation information. In a case where the ophthalmologic image is acquired by capturing of multiple images of the same location and addition processing (e.g., addition averaging processing) for the multiple images, the number (hereinafter referred to as an "addition number") of images used for the addition processing may be used as the evaluation information.

Specific contents of the medical data acquired based on the ophthalmologic image can be selected as necessary. For example, an automatic analysis result indicating whether or not the subject eye has some kind of disease may be acquired as the medical data from the ophthalmologic image. In this case, e.g., the probability of the presence of each disease may be acquired as the analysis result. The contents of the analysis result of the structure of the subject eye can be also selected as necessary. For example, from a laminagram image of the structure (e.g., the fundus) of the subject eye, an analysis result of at least any of a tissue layer and a layer boundary may be acquired as the medical data. From a fundus image of the subject eye, an analysis result of fundus blood vessels may be acquired as the medical data. In this case, the analysis result may include an analysis result (a discriminant result) of the arteries and veins of the fundus. The method for acquiring the image converted from the ophthalmologic image can be also selected as necessary. For example, from an ophthalmologic image with a low quality, high-quality image data may be acquired as converted image data. In this case, the high-quality image data may be, for example, acquired by reduction in ophthalmologic image noise, or may be acquired by improvement of the contrast of the ophthalmologic image. A high-resolution image with an enhanced resolution of the ophthalmologic image may be acquired as the converted image. An image with an enhanced visibility of the ophthalmologic image, an image with an emphasized particular structure on the ophthalmologic image or the like may be acquired as the converted image.

At the medical data acquisition step, the control section may acquire the medical data in such a manner that the ophthalmologic image is input to a mathematical model trained according to a machine learning algorithm. In this case, the mathematical model trained according to multiple pieces of training data is used, and therefore, even in a case where it is difficult to properly acquire the medical data with, e.g., a function not utilizing the machine learning algorithm, useful medical data is easily acquired.

In the case of utilizing the machine learning algorithm, as a difference between the quality of the ophthalmologic image used for training of the mathematical model and the quality of the ophthalmologic image input to the mathematical model increases, the reliability of the medical data output from the mathematical model is degraded. However, the ophthalmologic image processing apparatus of the present embodiment can change the medical data acquisition method according to the evaluation information indicating the appropriateness (e.g., the image quality) of the ophthalmologic image. Thus, the medical data useful for doctors or the like is more properly acquired.

Note that at the medical data acquisition step, the control section can also acquire the medical data from the ophthalmologic image without utilizing the machine learning algorithm. For example, even in a case where the above-described medical data is acquired in such a manner that ophthalmologic image processing is performed using a function without utilizing the machine learning algorithm, at least part of the technique described as an example in the present disclosure can be applied.

The control section may output the ophthalmologic image to other devices (e.g., a server) storing a program for implementing the mathematical model. The device as an ophthalmologic image output destination may input the ophthalmologic image, which has been input from the ophthalmologic image processing apparatus, to the mathematical model, thereby acquiring the medical data and outputting the acquired medical data to the ophthalmologic image processing apparatus. The control section may acquire the medical data input from the device as the ophthalmologic image output destination.

In the machine learning algorithm is utilized, the mathematical model may be trained using multiple training data sets of the ophthalmologic image captured by the ophthalmologic image capturing apparatus as input training data and the medical data corresponding to the input training data as output training data. The criterion for the evaluation may be set based on multiple pieces of input training data used for training of the mathematical model. In this case, the criterion for the evaluation information is properly set based on the multiple pieces of input training data used for training the mathematical model. For example, in a case where it is determined whether or not the quality of the ophthalmologic image input to the mathematical model is close to the image quality of the input training data, determination is more properly made using the set criterion.

A specific method for setting the criterion for the evaluation information based on the input training data can be also selected as necessary. For example, values (e.g., an average value and a standard deviation σ) indicating distribution of the evaluation information for the multiple pieces of input training data may be acquired, and a boundary indicating whether or not the evaluation information falls within a predetermined range (e.g., within a range of ±3 σ) set from the acquired values may be set as the criterion.

Note that the method for setting the criterion for the evaluation information can be also changed. For example, a fixed criterion may be set in advance. In a case where information indicating whether or not the medical data has been properly acquired from the ophthalmologic image is obtained for each ophthalmologic image, the criterion for the evaluation information may be set based on a relationship between the evaluation information on each ophthalmologic image and the information indicating whether or not the medical data has been properly acquired. Alternatively, the criterion may be set according to an instruction input from a user.

A criterion for comparing the evaluation information on the ophthalmologic image (i.e., a first criterion for determining the appropriateness for acquiring the medical data) and a criterion for determining whether or not the captured ophthalmologic image is appropriate as an image to be observed by the user (i.e., a second criterion for determining whether or not image capturing is successful) may be separately set. In this case, it is more properly determined whether or not the ophthalmologic image is appropriate. The control section may simultaneously or separately notify the user of information indicating whether or not the ophthalmologic image satisfies the first criterion and information indicating whether or not the ophthalmologic image satisfies the second criterion. In this case, the user can properly grasp the appropriateness of the ophthalmologic image according to a situation.

At the medical data acquisition step, the control section may acquire the utilized data in such a manner that information relating to the evaluation information on the ophthalmologic image is input to the mathematical model together with the ophthalmologic image. In this case, the medical data is output from the mathematical model, considering the evaluation information on the ophthalmologic image. Thus, the reliability of the output medical data is improved.

Note that in the case of inputting the information relating to the evaluation information to the mathematical model, the mathematical model may be trained in advance by many pieces of input training data different in the evaluation information from each other. In this case, the medical data is properly output from the mathematical model according to an algorithm corresponding to the evaluation information on the input ophthalmologic image.

The information input to the mathematical model and relating to the evaluation information may be the evaluation information itself or information (e.g., information indicating whether or not the evaluation information satisfies the criterion) obtained from the evaluation information.

At the medical data acquisition step, the control section may execute, for the ophthalmologic image, the evaluation information improvement processing of causing the evaluation information on the ophthalmologic image to approach the criterion in a case where the evaluation information on the ophthalmologic image does not satisfy the criterion. The control section may acquire the medical data based on an ophthalmologic image subjected to the evaluation information improvement processing. In this case, even in a case where the evaluation information (e.g., the image quality) on the ophthalmologic image acquired from the ophthalmologic image capturing apparatus does not satisfy the criterion, the medical data is acquired from the ophthalmologic image after the evaluation information improvement processing. Thus, the reliability of the acquired medical data is properly improved.

Note that specific contents of the evaluation information improvement processing can be selected as necessary. For example, at least any type of image processing such as well-known noise removal processing and sharpening processing may be executed for the ophthalmologic image. The evaluation information improvement processing for the ophthalmologic image may be executed utilizing the machine learning algorithm. The control section may execute the evaluation information improvement processing by means of data such as images or various measurement results of the same subject eye acquired by an apparatus different from the ophthalmologic image capturing apparatus having captured the ophthalmologic image.

At the medical data acquisition step, the control section may output an instruction for additionally capturing an image of the same location as that of the ophthalmologic image in a case where the evaluation information on the ophthalmologic image does not satisfy the criterion. The control section may acquire the medical data based on the additionally-captured ophthalmologic image. In this case, re-capturing of the ophthalmologic image of the same location is executed such that the evaluation information satisfies the criterion. Thus, the reliability of the acquired medical data is properly improved.

At the medical data acquisition step, the control section may output an instruction for additionally capturing an image of the same location as that of the ophthalmologic image in a case where the evaluation information on the ophthalmologic image does not satisfy the criterion. The control section may acquire the medical data based on an ophthalmologic image obtained by the addition averaging processing of the additionally-captured ophthalmologic image. In this case, the medical data is acquired based on the ophthalmologic image of which evaluation information has approached the criterion by the addition averaging processing. Thus, the reliability of the acquired medical data is properly improved. Note that the control section may execute the processing of capturing the image of the same location and the addition averaging processing for the additionally-captured image until the evaluation information satisfies the criterion. In this case, the reliability of the medical data is further improved.

The control section may acquire multiple ophthalmologic images of the same tissue of the same subject eye at the image acquisition step. The control section may acquire the medical data based on at least one, of which evaluation information satisfies the criterion, of the multiple ophthalmologic images. In this case, the ophthalmologic image used for acquiring the medical data is properly selected from the multiple ophthalmologic images of the same location based on the evaluation information. Thus, the reliability of the acquired medical data is properly improved.

At the medical data acquisition step, the control section may output warning information for the user in a case where the evaluation information on the ophthalmologic image does not satisfy the criterion. In this case, the user can properly make various types of determination such as the necessity of diagnosis or additional examination after having grasped that the ophthalmologic image evaluation information as the basis for acquiring the medical data does not satisfy the criterion.

Note that a specific method for outputting the warning information can be selected as necessary. For example, the control section may perform the processing of acquiring the medical data based on the ophthalmologic image only in a case where the evaluation information on the ophthalmologic image satisfies the criterion, and may output the warning information without performing the processing of acquiring the medical data based on the ophthalmologic image in a case where the evaluation information does not satisfy the criterion. In this case, the user can make various types of determination after having grasped from the warning information that the evaluation information on the ophthalmologic image does not satisfy the criterion (i.e., there is a probability that the reliability of the acquired medical data is degraded). In a case where the evaluation information does not satisfy the criterion, the control section may output the warning information, and may accept a user's instruction for whether or not the medical data is to be acquired from the ophthalmologic image of which evaluation information does not satisfy the criterion. In a case where an instruction for acquiring the medical data has been input, the control section may acquire the medical data based on the ophthalmologic image of which evaluation information does not satisfy the criterion.

Even in a case where the evaluation information on the ophthalmologic image does not satisfy the criterion, the control section may acquire the medical data based on the ophthalmologic image, and may output the acquired medical data together with the warning information. In this case, the user can easily grasp, from the warning information, that the medical data has been acquired based on the ophthalmologic image of which evaluation information does not satisfy the criterion.

A device executing the image acquisition step, the evaluation information acquisition step, and the medical data acquisition step can be selected as necessary. For example, a control section of a personal computer (hereinafter referred to as a "PC") may execute all of the image acquisition step, the evaluation information acquisition step, and the medical data acquisition step. That is, the control section of the PC may acquire the ophthalmologic image from the ophthalmologic image capturing apparatus, and may perform the processing of acquiring the evaluation information and the processing of acquiring the medical data based on the acquired ophthalmologic image. The control section of the ophthalmologic image capturing apparatus may execute all of the image acquisition step, the evaluation information acquisition step, and the medical data acquisition step. Control sections of multiple devices (e.g., the ophthalmologic image capturing apparatus, the PC or the like) may cooperate to execute the image acquisition step, the evaluation information acquisition step, and the medical data acquisition step.

BRIEF DESCRIPTION OF DRAWINGS

FIG. 10 is a flowchart of medical data acquisition processing executed by an ophthalmologic image processing system 100 of a fourth embodiment.

DESCRIPTION OF EMBODIMENTS (Apparatus Configuration)

Figure 1:
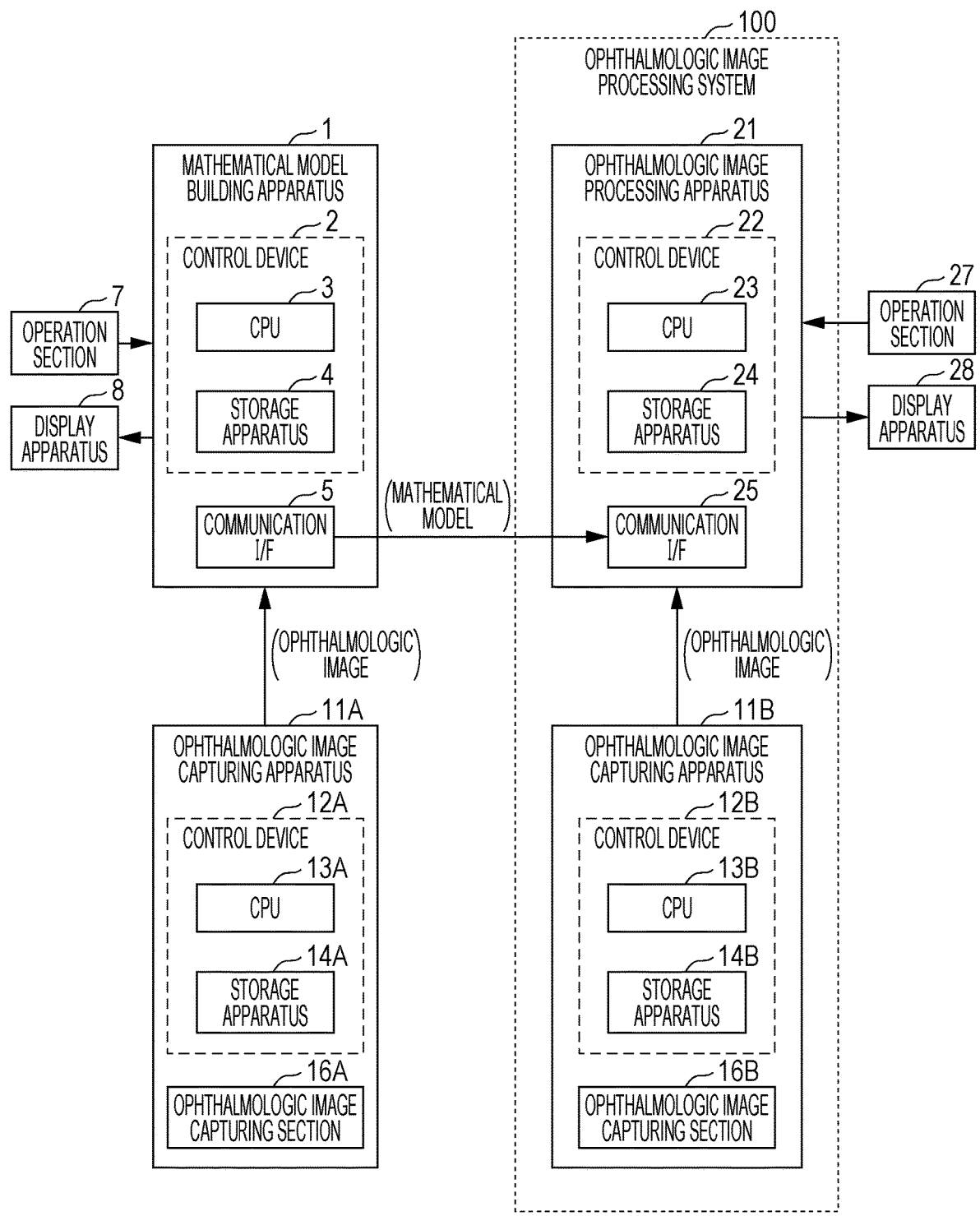
FIG. 1 is a block diagram showing outline configurations of a mathematical model building apparatus 1, an ophthalmologic image processing apparatus 21, and ophthalmologic image capturing apparatuses 11A, 11B.

Hereinafter, one typical embodiment in the present disclosure will be described with reference to the drawings. As shown in FIG. 1, in the present embodiment, a mathematical model building apparatus 1, an ophthalmologic image processing apparatus 21, and ophthalmologic image capturing apparatuses 11A, 11B are used. The mathematical model building apparatus 1 trains a mathematical model according to a machine learning algorithm to build the mathematical model. A program for implementing the built mathematical model is stored in a storage apparatus 24 of the ophthalmologic image processing apparatus 21. The ophthalmologic image processing apparatus 21 acquires medical data in such a manner that an ophthalmologic image is input to the mathematical model. The ophthalmologic image capturing apparatuses 11A, 11B capture ophthalmologic images as images of a tissue of a subject eye.

As one example, a personal computer (hereinafter referred to as a "PC") is used as the mathematical model building apparatus 1 of the present embodiment. Although details will be described later, the mathematical model building apparatus 1 trains the mathematical model by means of the ophthalmologic image (hereinafter referred to as a "training ophthalmologic image") acquired from the ophthalmologic image capturing apparatus 11A and the medical data corresponding to the training ophthalmologic image, thereby building the mathematical model. However, a device capable of functioning as the mathematical model building apparatus 1 is not limited to the PC. For example, the ophthalmologic image capturing apparatus 11A may function as the mathematical model building apparatus 1. Alternatively, control sections (e.g., a CPU of the PC and a CPU 13A of the ophthalmologic image capturing apparatus 11A) of multiple devices may cooperate to build the mathematical model.

In the present embodiment, an ophthalmologic image processing system 100 configured to acquire the medical data based on the ophthalmologic image includes the ophthalmologic image processing apparatus 21 as a PC and the ophthalmologic image capturing apparatus 11B. However, the configuration of the ophthalmologic image processing system can be changed. For example, one of the ophthalmologic image processing apparatus 21 or the ophthalmologic image capturing apparatus 11B may alone function as the ophthalmologic image processing system. The ophthalmologic image processing apparatus 21 may be a device (e.g., a mobile terminal such as a tablet terminal or a smartphone) other than the PC. Control sections of multiple devices may cooperate to function as the ophthalmologic image processing apparatus 21. A device (e.g., a server) different from the ophthalmologic image processing apparatus 21 may input the ophthalmologic image to the mathematical model to acquire the medical data. In this case, the ophthalmologic image processing apparatus 21 may acquire the medical data in such a manner that the ophthalmologic image is output to a device storing the program for implementing the mathematical model and the medical data is input from the device.

In the present embodiment, a case where a CPU is used as one example of a controller configured to perform various types of processing will be described as an example. Needless to say, a controller other than the CPU may be used for at least some of various types of processing. For example, a GPU may be employed as the controller so that the processing can be speeded up.

The mathematical model building apparatus 1 will be described. The mathematical model building apparatus 1 is arranged at, e.g., a manufacturer providing a user with the ophthalmologic image processing apparatus 21 or an ophthalmologic image processing program. The mathematical model building apparatus 1 includes a control device 2 configured to perform various types of control processing and a communication I/F 5. The control device 2 includes a CPU 3 as a controller in charge of control and a storage apparatus 4 capable of storing programs, data and the like. The storage apparatus 4 stores a mathematical model building program for executing later-described mathematical model building processing (see FIG. 2). The communication I/F 5 connects the mathematical model building apparatus 1 to other devices (e.g., the ophthalmologic image capturing apparatus 11A and the ophthalmologic image processing apparatus 21).

The mathematical model building apparatus 1 is connected to an operation section 7 and a display apparatus 8. The operation section 7 is operated by the user so that the user can input various instructions to the mathematical model building apparatus 1. As the operation section 7, at least any of a keyboard, a mouse, a touch panel and the like can be used, for example. Note that in addition to or instead of the operation section 7, e.g., a microphone for inputting various instructions may be used. The display apparatus 8 displays various images. As the display apparatus 8, various devices (e.g., at least any of a monitor, a display, a projector and the like.) capable of displaying images can be used. Note that an "image" in the present disclosure also includes a still image and a moving image.

The mathematical model building apparatus 1 can acquire ophthalmologic image data (hereinafter sometimes merely referred to as an "ophthalmologic image") from the ophthalmologic image capturing apparatus 11A. The mathematical model building apparatus 1 may acquire the ophthalmologic image data from the ophthalmologic image capturing apparatus 11A via at least any of wired communication, wireless communication, and a detachable storage medium (e.g., a USB memory), for example.

The ophthalmologic image processing apparatus 21 will be described. The ophthalmologic image processing apparatus 21 is arranged at, e.g., a facility (e.g., a hospital or a medical examination facility) for diagnosis or examination of a subject. The ophthalmologic image processing apparatus 21 includes a control device 22 configured to perform various types of control processing and a communication I/F 25. The control device 22 includes a CPU 23 as a controller in charge of control and the storage apparatus 24 capable of storing programs, data and the like. The storage apparatus 24 stores the ophthalmologic image processing program for executing later-described ophthalmologic image processing (see FIG. 6). The ophthalmologic image processing program includes the program for implementing the mathematical model built by the mathematical model building apparatus 1. The communication I/F 25 connects the ophthalmologic image processing apparatus 21 to other devices (e.g., the ophthalmologic image capturing apparatus 11B and the mathematical model building apparatus 1).

The ophthalmologic image processing apparatus 21 is connected to an operation section 27 and a display apparatus 28. As the operation section 27 and the display apparatus 28, various devices can be used as in the operation section 7 and the display apparatus 8 described above.

The ophthalmologic image processing apparatus 21 can acquire the ophthalmologic image from the ophthalmologic image capturing apparatus 11B. The ophthalmologic image processing apparatus 21 may acquire the ophthalmologic image from the ophthalmologic image capturing apparatus 11B via at least any of wired communication, wireless communication, and a detachable storage medium (e.g., a USB memory), for example. The ophthalmologic image processing apparatus 21 may acquire the program for implementing the mathematical model built by the mathematical model building apparatus 1 via communication, for example.

The ophthalmologic image capturing apparatuses 11A, 11B will be described. As one example, a case where the ophthalmologic image capturing apparatus 11A providing the ophthalmologic image to the mathematical model building apparatus 1 and the ophthalmologic image capturing apparatus 11B providing the ophthalmologic image to the ophthalmologic image processing apparatus 21 are used will be described in the present embodiment. However, the number of ophthalmologic image capturing apparatuses to be used is not limited to two. For example, the mathematical model building apparatus 1 and the ophthalmologic image processing apparatus 21 may acquire ophthalmologic images from multiple ophthalmologic image capturing apparatuses. Alternatively, the mathematical model building apparatus 1 and the ophthalmologic image processing apparatus 21 may acquire an ophthalmologic image from a single common ophthalmologic image capturing apparatus.

In the present embodiment, an OCT apparatus will be described as an example of an ophthalmologic image capturing apparatus 11 (11A, 11B). Note that an ophthalmologic image capturing apparatus (e.g., a laser scanning optometry apparatus (a scanning laser ophthalmoscopy: SLO), a fundus camera, a shineproof camera, or a corneal endothelium image capturing apparatus (a corneal endothelium medium: CEM)) other than the OCT apparatus may be used.

The ophthalmologic image capturing apparatus 11 (11A, 11B) includes a control device 12 (12A, 12B) configured to perform various types of control processing and an ophthalmologic image capturing section 16 (16A, 16B). The control device 12 includes a CPU 13 (13A, 13B) as a controller in charge of control and a storage apparatus 14 (14A, 14B)

capable of storing programs, data and the like. In a case where at least part of the later-described ophthalmologic image processing (see FIG. 4) is executed by the ophthalmologic image capturing apparatus 11, at least part of the ophthalmologic image processing program for executing the ophthalmologic image processing is stored in the storage apparatus 14, needless to say.

The ophthalmologic image capturing section 16 includes various configurations necessary for capturing the ophthalmologic image of the subject eye. The ophthalmologic image capturing section 16 of the present embodiment includes, for example, an OCT light source, a branch optical element configured to branch OCT light emitted from the OCT light source into measurement light and reference light, a scanning section for performing scanning with the measurement light, an optical system for irradiating the subject eye with the measurement light, and a light receiving element configured to receive synthetic light of light reflected on the tissue of the subject eye and the reference light.

The ophthalmologic image capturing apparatus 11 is capable of capturing a two-dimensional laminagram image and a three-dimensional laminagram image of the fundus of the subject eye. Specifically, the CPU 13 scans a scan line with the OCT light (the measurement light), thereby capturing a two-dimensional laminagram image (see FIGS. 3 and 5) of a section crossing the scan line. Moreover, the CPU 13 performs two-dimensional scanning with the OCT light, thereby capturing a three-dimensional laminagram image of the tissue. For example, the CPU 13 scans, with the measurement light, each of multiple scan lines different in position from each other in a two-dimensional region when the tissue is viewed from the front, thereby acquiring multiple two-dimensional laminagram images. Subsequently, the CPU 13 combines the multiple captured two-dimensional laminagram images, thereby acquiring a three-dimensional laminagram image.

Further, the CPU 13 scans, with the measurement light, the same location (in the present embodiment, the same scan line) of the tissue multiple times, thereby capturing multiple ophthalmologic images of the same location. The CPU 13 performs addition averaging processing for the multiple ophthalmologic images of the same location, thereby acquiring an addition-averaged image with reduced influence of speckle noise. The addition averaging processing may be, for example, performed in such a manner that pixel values of pixels of the multiple ophthalmologic images at the same position are averaged. As the number of images subjected to the addition averaging processing increases, the influence of the speckle noise is more easily reduced, but an image capturing time increases. Note that the ophthalmologic image capturing apparatus 11 executes the tracking processing of causing an OCT light scanning position to follow motion of the subject eye while capturing the multiple ophthalmologic images of the same location.

(Mathematical Model Building Processing)

The mathematical model building processing executed by the mathematical model building apparatus 1 will be described with reference to FIGS. 2 to 5. The mathematical model building processing is executed by the CPU 3 according to the mathematical model building program stored in the storage apparatus 4.

In the mathematical model building processing, the mathematical model for outputting the medical data based on the ophthalmologic image is built in such a manner that the mathematical model is trained using a training data set. The training data set includes input-side data (input training data) and output-side data (output training data). Various types of medical data can be output from the mathematical model. According to the type of medical data output from the mathematical model, the type of training data set used for training of the mathematical model is set. Hereinafter, one example of a relationship between the type of medical data to be output and the training data set used for training of the mathematical model will be described.

Figure 3:
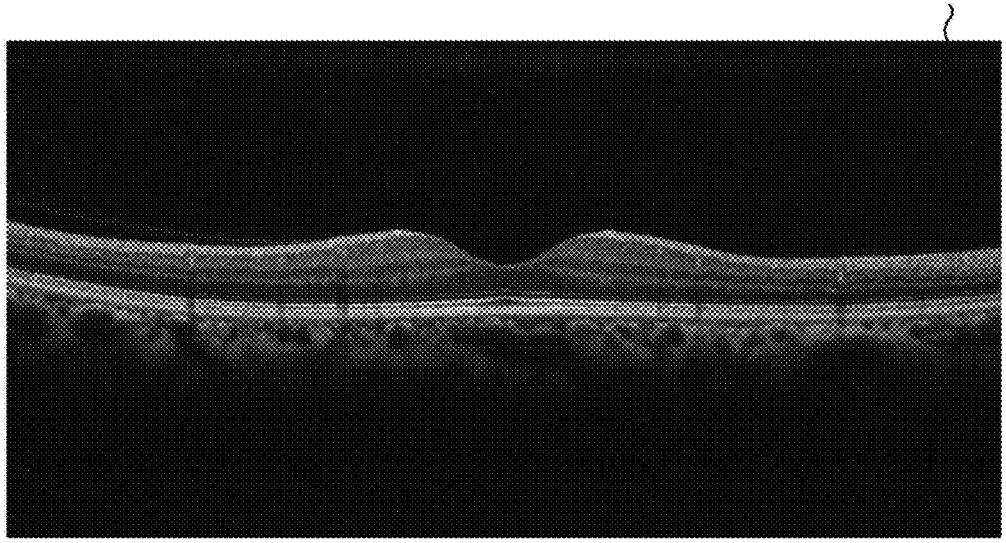
FIG. 3 is an image showing one example of input training data in a case where an analysis result of the structure of a fundus tissue of a subject eye is output to a mathematical model.
Figure 4:
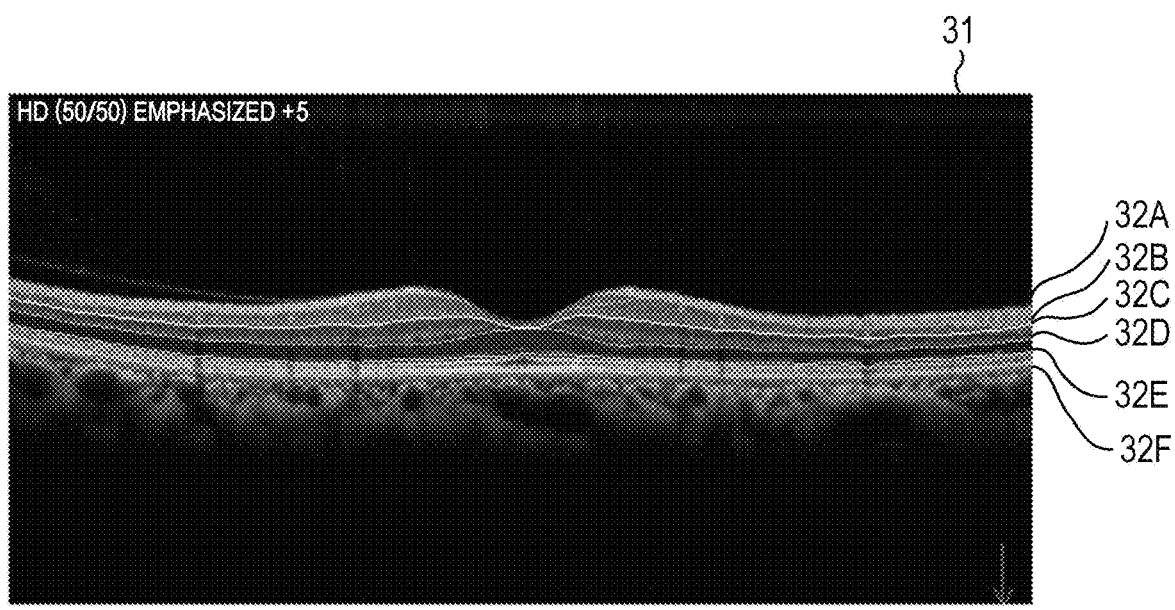
FIG. 4 is an image showing one example of output training data in a case where the analysis result of the structure of the fundus tissue of the subject eye is output to the mathematical model.

First, a case where an analysis result of the structure of the tissue of the subject eye is output from the mathematical model in such a manner that the ophthalmologic image is input to the mathematical model will be described. In this case, the mathematical model is trained using the ophthalmologic image of the tissue of the subject eye as the input training data and the medical data indicating the structure of the tissue shown in the input training data (the ophthalmologic image) as the output training data. FIGS. 3 and 4 show one example of the input training data and the output training data in a case where the analysis result of the structure of the fundus tissue of the subject eye is, as the medical data, output from the mathematical model. Input training data 30 shown as an example in FIG. 3 is a two-dimensional laminagram image of the fundus tissue. The input training data 30 shows multiple layers of the fundus tissue. Moreover, output training data 31 shown as an example in FIG. 4 shows the position of the structure of the tissue shown in the input training data 30. As one example, the output training data 31 shown as the example in FIG. 4 includes data with labels 32A to 32F each indicating the positions of six boundaries shown in the input training data 30 (see FIG. 3). As a result, when the ophthalmologic image is input to the trained mathematical model, an analysis result of at least any of tissue layers and boundaries is output as the medical data. In the present embodiment, the data with the labels 32A to 32F in the output training data 31 is generated in such a manner that an operating person operates the operation section 7 while viewing the boundaries in the input training data 30. Note that the method for generating the data with the labels can be changed.

Note that an analysis result of the structure of the tissue of the subject eye other than the layers and the boundaries can be also output from the mathematical model. For example, an analysis result of the fundus blood vessels of the subject eye can be also output from the mathematical model. Further, an analysis result of the arteries and veins of the fundus can be also output from the mathematical model. In this case, the mathematical model may be trained using an ophthalmologic image including the fundus blood vessels as the input training data and data indicating the position of each blood vessel (the arteries and the veins) shown in the input training data as the output training data. An analysis result of, e.g., the maculae or fovea of the fundus can be also output from the mathematical model. The input training data is not necessarily the laminagram image of the tissue of the subject eye, and may be a two-dimensional front image, for example.

Figure 5:
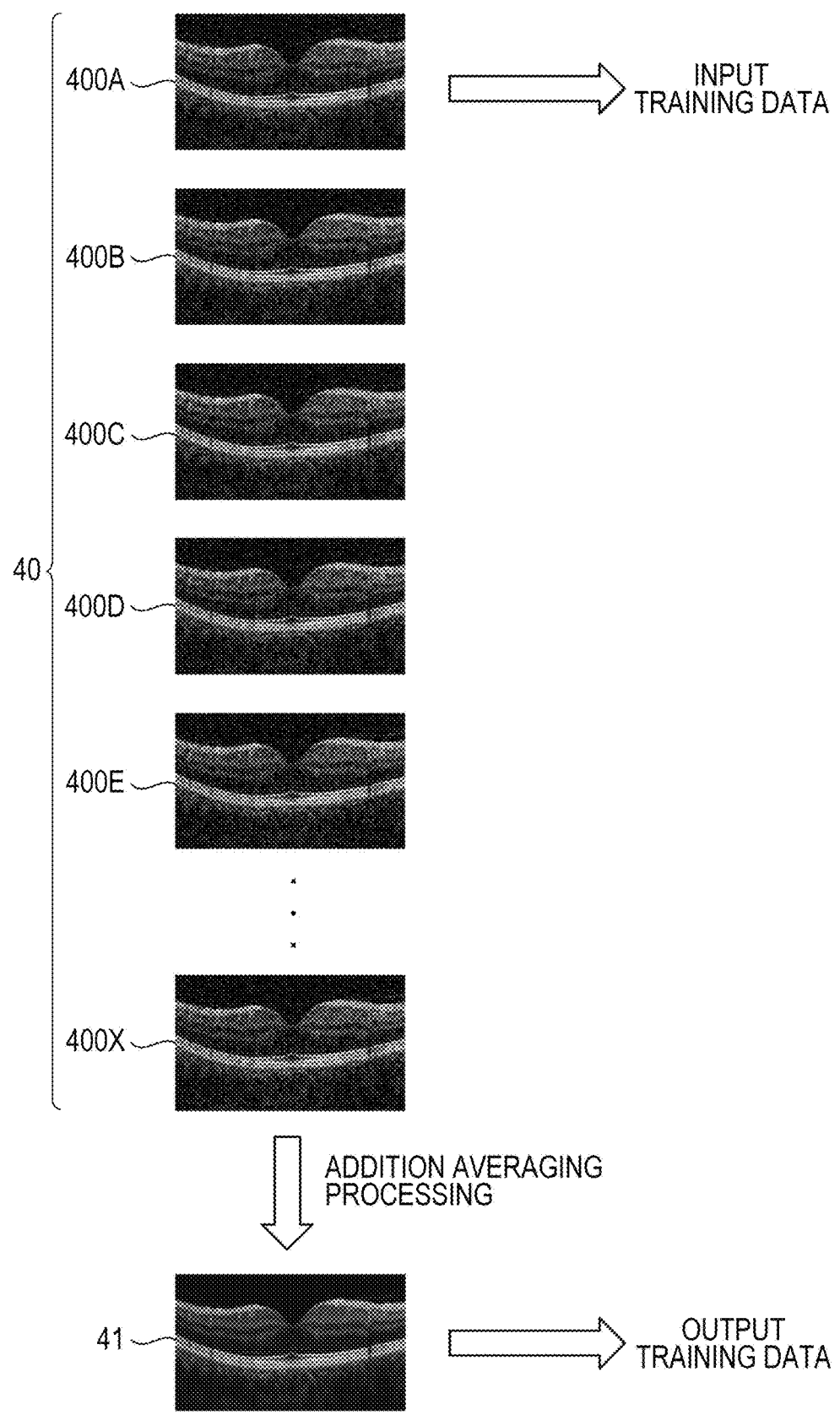
FIG. 5 is an image showing one example of the input training data and the output training data in a case where a converted image is output from the mathematical model.

Next, a case where an image converted from the input image is output from the mathematical model in such a manner that the ophthalmologic image is input to the mathematical model will be described. As described above, the converted image is, for example, at least any of an image with reduced noise of the input ophthalmologic image, an image with an enhanced resolution of the ophthalmologic image, an image with the improved visibility of the ophthalmologic image, and an image with an emphasized particular structure on the ophthalmologic image. As one example, in the present embodiment, the mathematical model is trained using the ophthalmologic image of the tissue of the subject eye as the input training data and the ophthalmologic image of the same location with a higher image quality (e.g., reduced noise) than that of the input training data as the output training data. FIG. 5 shows one example of the input training data and the output training data in a case where the converted image is output from the mathematical model. In the example shown in FIG. 5, the CPU 3 acquires a set 40 of multiple training ophthalmologic images 400A to 400X of the same location of the tissue. The CPU 3 takes, as the input training data, some (the number of images smaller than that used for addition averaging of the output training data as described later) of the multiple training ophthalmologic images 400A to 400X of the set 40. Moreover, the CPU 3 acquires, as the output training data, an addition-averaged image 41 of the multiple training ophthalmologic images 400A to 400X of the set 40. In a case where the mathematical model is trained using the input training data and the output training data shown as the example in FIG. 5, the high-quality converted image with reduced influence of the speckle noise is output in such a manner that the ophthalmologic image is input to the trained mathematical model.

Note that the method for generating the high-quality output training data can be changed. For example, the output training data may be generated in such a manner that the image quality of the input training data is improved by processing other than the addition averaging processing. The type of output training data may be selected as necessary according to the type of converted image output from the mathematical model. The input training data is not limited to the laminagram image of the tissue.

Next, a case where an automatic analysis result indicating whether or not the subject eye has some kind of disease is output from the mathematical model in such a manner that the ophthalmologic image is input to the mathematical model will be described. In this case, the mathematical model is trained using the ophthalmologic image of the tissue of the subject eye as the input training data and data indicating the presence or absence of a disease in an image capturing target shown in the input training data as the output training data, for example.

Figure 2:
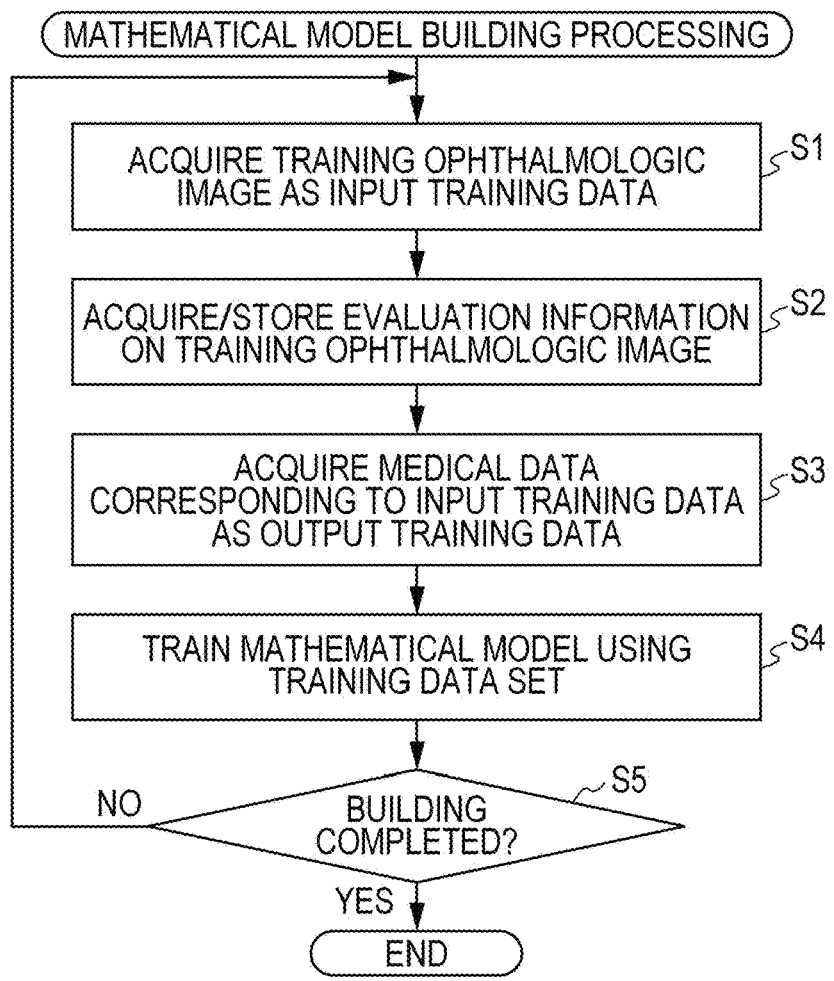
FIG. 2 is a flowchart of mathematical model building processing executed by the mathematical model building apparatus 1.

The mathematical model building processing will be described with reference to FIG. 2. The CPU 3 acquires, as the input training data, data of the ophthalmologic image (the training ophthalmologic image) captured by the ophthalmologic image capturing apparatus 11A (S1). In the present embodiment, the data of the training ophthalmologic image is generated by the ophthalmologic image capturing apparatus 11A, and thereafter, is acquired by the mathematical model building apparatus 1. However, the CPU 3 may acquire the data of the training ophthalmologic image in such a manner that a signal (e.g., an OCT signal) to be a basis for generating the training ophthalmologic image is acquired from the ophthalmologic image capturing apparatus 11A and the training ophthalmologic image is generated based on the acquired signal.

Subsequently, the CPU 3 acquires evaluation information on the training ophthalmologic image acquired at S1, and stores the evaluation information in the storage apparatus 4 (S2). The evaluation information indicates a degree (an appropriateness) indicating whether or not the ophthalmologic image is appropriate for acquiring the above-described medical data. Generally, as the quality of the ophthalmologic image increases, the medical data is more appropriately obtained from the ophthalmologic image. Thus, in the present disclosure, a value relating to the quality of the ophthalmologic image is, as one example, used as the evaluation information on the ophthalmologic image. For example, an index (e.g., a signal strength index (SSI) or a quality index (QI)) indicating the strength of the signal of the ophthalmologic image or the goodness of the signal may be used as the evaluation information on the ophthalmologic image. Alternatively, at least any of the ratio (a signal to noise ratio (SNR) of a noise level to an image signal level, a background noise level, an image contrast and the like may be used as the evaluation information on the ophthalmologic image. Alternatively, an image capturing condition (e.g., at least any of a condition relating to scanning, an exposure time and the like when the ophthalmologic image is captured by scanning of the tissue with light) when the ophthalmologic image is captured by the ophthalmologic image capturing apparatus 11A may be used as the evaluation information. In a case where the ophthalmologic image is acquired by the above-described addition averaging processing, the number (hereinafter referred to as an "addition number") of images used for the addition averaging processing may be used as the evaluation information.

Subsequently, the CPU 3 acquires, as the output training data, the medical data corresponding to the input training data acquired at S1 (S3). One example of a correspondence between the input training data and the output training data (the medical data) is as described above.

Subsequently, the CPU 3 executes, according to the machine learning algorithm, training of the mathematical model by means of the training data set (S4). For example, as the machine learning algorithm, a neural network, a random forest, boosting, or a support vector machine (SVM) has been generally known.

The neural network is the technique of mimicking behavior of a neuronal network of a living organism. Examples of the neural network include a feedforward neural network, a radial basis function (RBF) network, a spiking neural network, a convolutional neural network, a recurrent neural net (e.g., a feedback neural net), and a stochastic neural network (e.g., a Boltzmann machine and a Bayesian network).

The random forest is a method in which many decision trees are generated by learning based on randomly-sampled training data. In the case of using the random forest, the average of results obtained from each decision tree is taken (or a decision by majority is made) by following branches of the multiple decision trees learnt in advance as classifiers.

The boosting is the technique of combining multiple weak classifiers to generate a strong classifier. The simple weak classifiers successively learn to build the strong classifier.

The SVM is the technique of forming two classes of pattern classifiers by means of a linear input element. The SVM learns a parameter for the linear input element according to a basis (the hyperplane separation theorem) that a maximum-margin hyperplane that a distance to each data point is maximum is obtained from the training data, for example.

The mathematical model indicates, for example, a data structure for predicting a relationship between input data and output data. The mathematical model is built by training with the training data set. As described above, the training data set is a set of the input training data and the output training data. For example, correlation data (e.g., a weight) between the input and the output is updated by training.

In the present embodiment, a multilayered neural network is used as the machine learning algorithm. The neural network includes an input layer for inputting data, an output layer for generating data to be predicted, and one or more hidden layers between the input layer and the output layer.

Multiple nodes (also called units) are arranged at each layer. Specifically, in the present embodiment, the convolutional neural network (CNN) as one type of the multilayered neural network is used. Note that other machine learning algorithms may be used. For example, generative adversarial networks (GAN) utilizing two competitive neural networks may be employed as the machine learning algorithm.

Until building of the mathematical model is completed (S5: NO), the processing of S1 to S4 is repeated. When building of the mathematical model is completed (S5: YES), the mathematical model building processing ends. The program and data for implementing the built mathematical model are incorporated into the ophthalmologic image processing apparatus 21.

(Ophthalmologic Image Processing)

The ophthalmologic image processing executed by the ophthalmologic image processing system 100 will be described with reference to FIGS. 6 to 10. In the ophthalmologic image processing, the medical data for the subject eye shown on the ophthalmologic image is acquired based on the ophthalmologic image. In the present embodiment, a case where the ophthalmologic image processing apparatus 21 included in the ophthalmologic image processing system 100 executes the ophthalmologic image processing shown as an example in FIGS. 6 to 10 will be described as an example. However, as described above, CPUs (e.g., the CPU 13B of the ophthalmologic image capturing apparatus 11B) of other devices included in the ophthalmologic image processing system 100 may execute the ophthalmologic image processing. Alternatively, multiple control sections (e.g., the CPU 23 of the ophthalmologic image processing apparatus 21 and the CPU 13B of the ophthalmologic image capturing apparatus 11B) included in the ophthalmologic image processing system 100 may cooperate to execute the ophthalmologic image processing. The ophthalmologic image processing of the present embodiment is executed by the CPU 23 according to the ophthalmologic image processing program stored in the storage apparatus 24.

Figure 6:
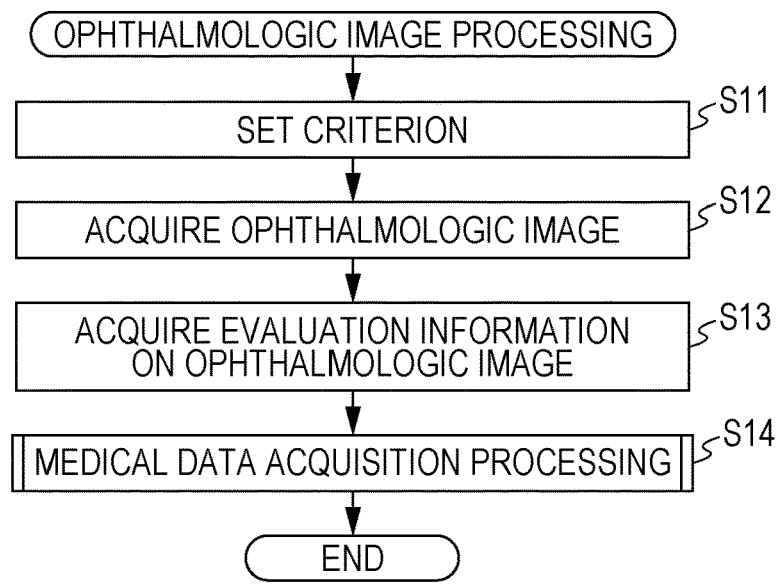
FIG. 6 is a flowchart of ophthalmologic image processing executed by an ophthalmologic image processing system 100.

As shown in FIG. 6, the CPU 23 sets a criterion relating to the evaluation information on the ophthalmologic image (S11). Although details will be described later, the CPU 23 changes the method for acquiring the medical data according to whether or not the evaluation information on the ophthalmologic image for acquiring the medical data satisfies the criterion. In the present embodiment, when it is determined whether or not the ophthalmologic image for acquiring the medical data is appropriate for acquiring the medical data, the evaluation information on the ophthalmologic image is compared with the criterion.

As one example, at S1 of the present embodiment, the criterion for the evaluation information is set based on multiple pieces of input training data used for training of the mathematical model. The evaluation information for the input training data used for training of the mathematical model is stored in the above-described mathematical model building processing (S2 of FIG. 2). The CPU 23 sets the criterion based on the stored evaluation information for the input training data. A specific method for setting the criterion can be selected as necessary. As one example, in the present embodiment, the CPU 23 acquires values (an average value and a standard deviation a) indicating distribution of the evaluation information for the multiple pieces of input training data, and sets, as the criterion, a boundary value indicating whether or not the evaluation information falls within a predetermined range (e.g., within a range of ±3 a) set from the acquired values. However, the method for setting the criterion can be changed. For example, the CPU 23 may set the criterion according to an instruction input from the user. A control section (e.g., the CPU 3 of the mathematical model building apparatus 1) of a device other than the ophthalmologic image processing apparatus 21 may set the criterion for the evaluation information. Alternatively, a fixed criterion may be set in advance. In the present embodiment, a criterion for comparing the evaluation information on the ophthalmologic image (i.e., a first criterion for determining the appropriateness for acquiring the medical data) and a criterion for determining whether or not the captured ophthalmologic image is appropriate as an image to be observed by the user (i.e., a second criterion for determining whether or not image capturing is successful) are separately set. The CPU 23 can simultaneously or separately notify the user of information indicating whether or not the ophthalmologic image satisfies the first criterion and information indicating whether or not the ophthalmologic image satisfies the second criterion (e.g., displays the information on the display apparatus 28).

Subsequently, the CPU 23 acquires the ophthalmologic image of the subject eye captured by the ophthalmologic image capturing apparatus 11B (S12). The ophthalmologic image acquired at S12 is the same type of image as the ophthalmologic image used as the input training data in training of the mathematical model. That is, in a case where the two-dimensional laminagram image is used as the input training data, the ophthalmologic image acquired at S12 is also a two-dimensional laminagram image. In a case where the two-dimensional front image is used as the input training data, the ophthalmologic image acquired at S12 is also a two-dimensional front image. Note that at S12, multiple ophthalmologic images targeted for the same subject eye are acquired in some cases, and a single ophthalmologic image is acquired in other cases.

Subsequently, the CPU 23 acquires the evaluation information on the ophthalmologic image acquired at S12 (S13). As described above, the evaluation information indicates the degree (the appropriateness) indicating whether or not the ophthalmologic image is appropriate for acquiring the medical data. In the present embodiment, various values relating to the quality of the ophthalmologic image can be used as the evaluation information as described above.

Subsequently, the CPU 23 acquires the medical data based on the ophthalmologic image acquired at S12 (S14). At S14, the method for acquiring the medical data is changed according to whether or not the evaluation information acquired at S13 satisfies the criterion. Hereinafter, medical data acquisition processing in each of first to fourth embodiments will be described in detail with reference to FIGS. 7 to 10.

First Embodiment

Figure 7:
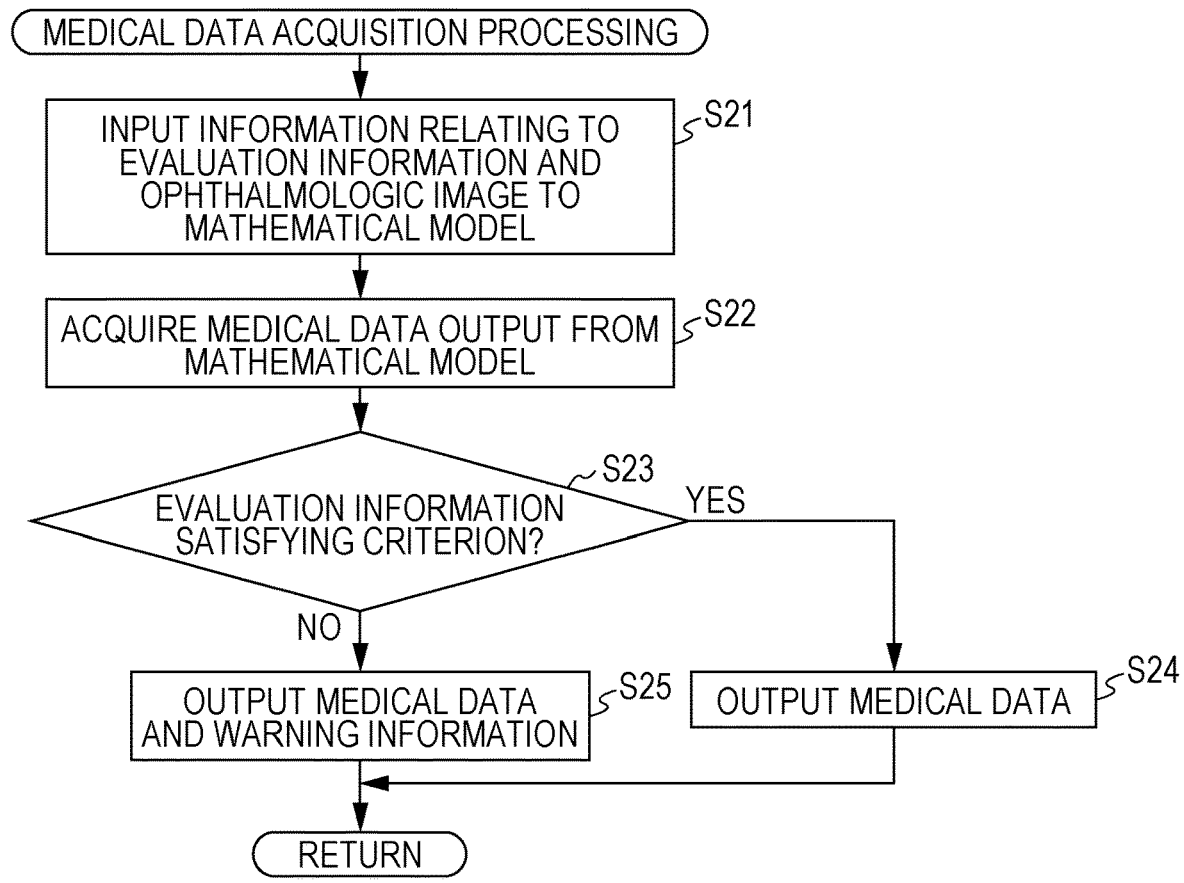
FIG. 7 is a flowchart of medical data acquisition processing executed by an ophthalmologic image processing system 100 of a first embodiment.

The medical data acquisition processing executed by an ophthalmologic image processing system 100 in the first embodiment will be described with reference to FIG. 7. In the first embodiment, information relating to evaluation information on an ophthalmologic image is input to a mathematical model together with the ophthalmologic image, and in this manner, the reliability of medical data is improved. In a case where the evaluation information on the ophthalmologic image does not satisfy a criterion, warning information for a user is output.

First, a CPU 23 inputs the information relating to the evaluation information and the ophthalmologic image to the mathematical model (S21). The information relating to the evaluation information may be the evaluation information itself acquired at S3 of FIG. 6 or information (e.g., information indicating whether or not the evaluation information satisfies the criterion) obtained from the evaluation information acquired at S3. Note that the mathematical model in the first embodiment is trained in advance by many pieces of input training data different in the evaluation information from each other in mathematical model building processing (see FIG. 2). When the information relating to the evaluation information and the ophthalmologic image are input to the mathematical model, the mathematical model outputs the medical data according to an algorithm corresponding to the evaluation information on the ophthalmologic image. Thus, a difference between the input training data evaluation information used for building the algorithm and the ophthalmologic image evaluation information input to the mathematical model is less likely to be caused. Thus, the reliability of the medical data is likely to be improved.

The CPU 23 acquires the medical data output from the mathematical model (S22). The CPU 23 determines whether or not the ophthalmologic image evaluation information input to the mathematical model at S21 satisfies the criterion (S23). In a case where the evaluation information satisfies the criterion (S23: YES), the reliability of the medical data acquired at S22 is high in many cases. Thus, the CPU 23 directly outputs the medical data acquired at S22 (S24). On the other hand, in a case where the evaluation information does not satisfy the criterion (S23: NO), there is a probability that the reliability of the medical data acquired at S22 is low. Thus, the CPU 23 outputs the medical data acquired at S22 together with the warning information for warning the user (S25). As a result, the user can easily grasp, from the warning information, that the medical data has been acquired based on the ophthalmologic image of which evaluation information does not satisfy the criterion.

Second Embodiment

Figure 8:
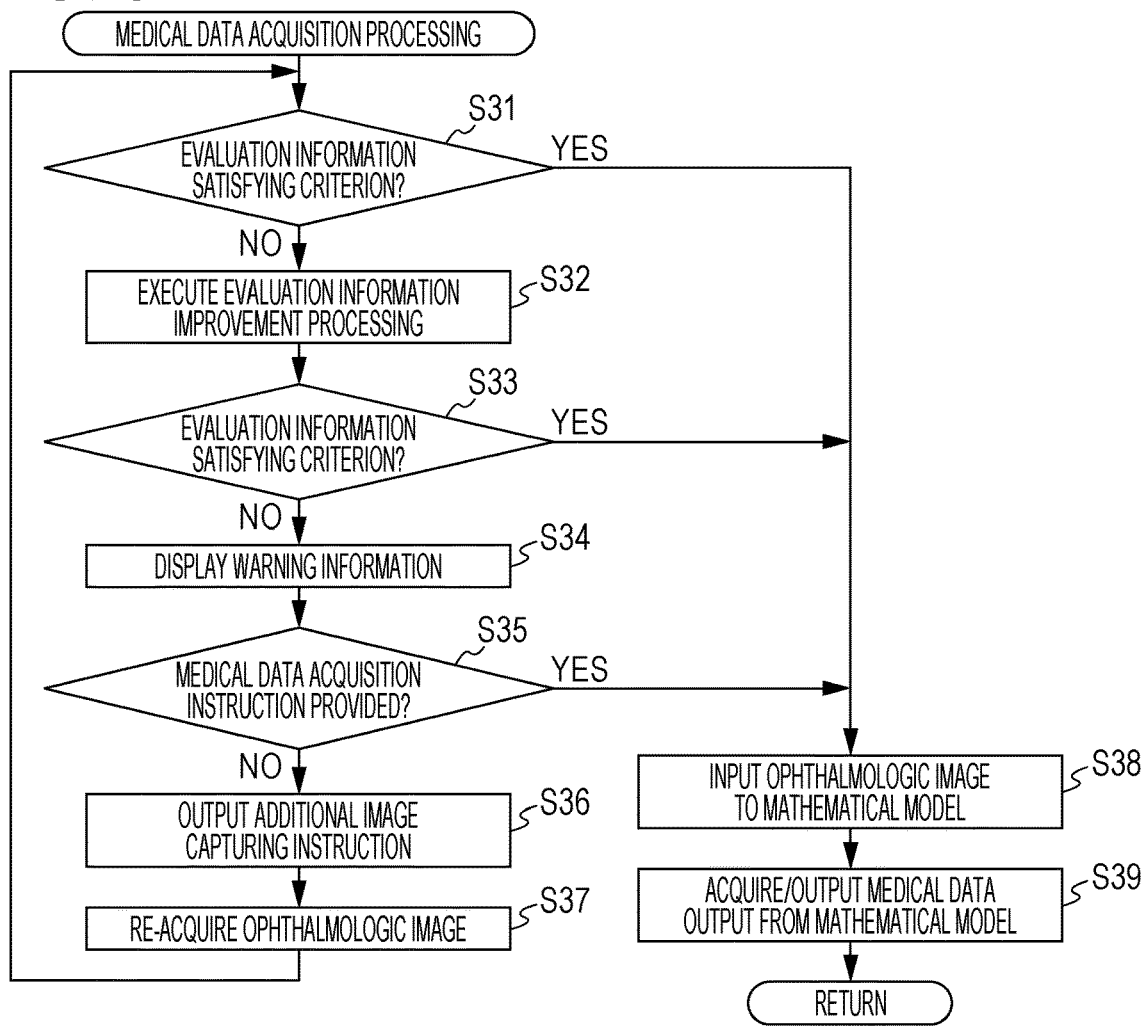
FIG. 8 is a flowchart of medical data acquisition processing executed by an ophthalmologic image processing system 100 of a second embodiment.

The medical data acquisition processing executed by an ophthalmologic image processing system 100 in the second embodiment will be described with reference to FIG. 8. In the second embodiment, in a case where evaluation information on an ophthalmologic image does not satisfy a criterion, evaluation information improvement processing (as one example, image quality improvement processing in the present embodiment) for the ophthalmologic image is executed. Accordingly, the reliability of medical data is improved. Moreover, in a case where the evaluation information on the ophthalmologic image does not satisfy the criterion, warning information for a user is output before the medical data is acquired. Further, in a case where the evaluation information on the ophthalmologic image does not satisfy the criterion, additional image capturing is performed for the same location of a subject eye, and an ophthalmologic image is acquired again.

First, a CPU 23 determines whether or not the evaluation information on the ophthalmologic image satisfies the criterion (S31). In a case where the evaluation information satisfies the criterion (S31: YES), the ophthalmologic image is input to a mathematical model (S38), and the medical data output from the mathematical model is acquired and output (S39).

In a case where the evaluation information does not satisfy the criterion (S31: NO), the CPU 23 executes, for the ophthalmologic image for acquiring the medical data, the evaluation information improvement processing for causing the evaluation information to approach the criterion is executed (S32). In the present embodiment, the CPU 23 executes, as one example of the evaluation information improvement processing, the image quality improvement processing for improving image quality. For example, as the image quality improvement processing, at least any of well-known noise removal processing, sharpening processing and the like can be employed. The evaluation information improvement processing for the ophthalmologic image may be performed utilizing a machine learning algorithm. Alternatively, the CPU 23 may execute the evaluation information improvement processing for the ophthalmologic image by means of images or various measurement results of the same subject eye acquired by an apparatus (in the present embodiment, an ophthalmologic image capturing apparatus other than an OCT apparatus) different from an ophthalmologic image capturing apparatus 11B.

The CPU 23 acquires the ophthalmologic image evaluation information subjected to the evaluation information improvement processing, and determines whether or not the evaluation information satisfies the criterion (S33). In a case where the evaluation information satisfies the criterion (S33: YES), the ophthalmologic image is input to the mathematical model (S38), and the medical data output from the mathematical model is acquired and output (S39).

In a case where the evaluation information does not satisfy the criterion (S33: NO), the CPU 23 outputs the warning information for the user without performing the processing (S38, S39) of acquiring the medical data (S34). The warning information may be output by being displayed on a display apparatus 28, or may be output via audio.

Subsequently, the CPU 23 determines whether or not an instruction for acquiring the medical data from the ophthalmologic image of which evaluation information does not satisfy the criterion has been input from the user (S35). In the present embodiment, in a case where the evaluation information on the ophthalmologic image does not satisfy the criterion, the user can input, via, e.g., an operation section 27, the instruction for acquiring the medical data from the ophthalmologic image not satisfying the criterion or an instruction for executing additional ophthalmologic image capturing for the same subject eye. In a case where the instruction for acquiring the medical data has been input (S35: YES), the ophthalmologic image is input to the mathematical model (S38), and the medical data output from the mathematical model is acquired and output (S39). On the other hand, in a case where the additional image capturing execution instruction has been input (S35: NO), the CPU 23 outputs the instruction for additionally capturing an image of the same location to the ophthalmologic image capturing apparatus 11B (S36). The CPU 23 acquires the additionally-captured ophthalmologic image again (S37). Thereafter, the processing returns to S31. If the ophthalmologic image of which evaluation information has approached the criterion is acquired again at S37, the reliability of the medical data acquired at S38, S39 is improved.

Third Embodiment

The medical data acquisition processing executed by an ophthalmologic image processing system 100 in the third embodiment will be described with reference to FIG. 9. In the third embodiment, in a case where evaluation information on an ophthalmologic image does not satisfy a criterion, an image of the same location of a subject eye is additionally captured, and addition averaging processing for an original ophthalmologic image is performed. As a result, the reliability of acquired medical data is improved.

First, a CPU 23 determines whether or not the evaluation information on the ophthalmologic image satisfies the criterion (S41). In a case where the evaluation information satisfies the criterion (S41: YES), the ophthalmologic image is input to a mathematical model (S44), and the medical data output from the mathematical model is acquired and output (S45).

In a case where the evaluation information on the ophthalmologic image does not satisfy the criterion (S41: NO), the CPU 23 outputs, to an ophthalmologic image capturing apparatus 11B, an instruction for additionally capturing an image of the same location as that of the original ophthalmologic image (the image acquired at S12 of FIG. 6) (S42). Subsequently, the CPU 23 executes, for the original ophthalmologic image, the addition averaging processing for the additionally-captured ophthalmologic image (S42). As described above, as the number of images used for the addition averaging processing increases, image quality is improved. The addition averaging processing may be executed by the ophthalmologic image capturing apparatus 11B, or may be executed by an ophthalmologic image processing apparatus 21. The processing returns to S41, and additional image capturing (S42) and the addition averaging processing (S43) are repeated until the evaluation information satisfies the criterion. When the evaluation information satisfies the criterion (S41: YES), the medical data is acquired using the ophthalmologic image generated with the improved evaluation information by the addition averaging processing (S44, S45).

Fourth Embodiment

The medical data acquisition processing executed by an ophthalmologic image processing system 100 in the fourth embodiment will be described with reference to FIG. 10. In the fourth embodiment, medical data is acquired based on ophthalmologic images of which evaluation information satisfies a criterion among multiple ophthalmologic images captured from the same tissue of the same subject eye. In the fourth embodiment, in the processing of S12 of FIG. 6, the multiple ophthalmologic images of the same tissue of the same subject eye are acquired.

First, a CPU 23 determines whether or not there are the ophthalmologic images of which evaluation information satisfies the criterion among the multiple ophthalmologic images acquired at S12 of FIG. 6 (S51). In a case where there are no ophthalmologic images of which evaluation information satisfies the criterion (S51: NO), e.g., output of warning information (e.g., see S34 of FIG. 8) and additional image capturing processing (e.g., see S35 to S37 of FIG. 8) are executed as necessary. In a case where there are the ophthalmologic images of which evaluation information satisfies the criterion (S51: YES), the CPU 23 inputs at least any of the ophthalmologic images satisfying the criterion to a mathematical model (S52). The medical data output from the mathematical model is acquired and output (S53).

The techniques disclosed in the above-described embodiments are mere examples. Thus, the techniques described as the examples in the above-described embodiments can be changed. First, only some of the multiple techniques described as the examples in the above-described embodiments can be executed. For example, in the medical data acquisition processing (see FIG. 7) in the first embodiment, the processing of inputting the information relating to the evaluation information to the mathematical model together with the ophthalmologic image (S21) and the processing of outputting the warning information (S25) are both executed. However, only one of S21 or S25 may be executed. Similarly, in the medical data acquisition processing (see FIG. 8) in the second embodiment, the evaluation information improvement processing (S31, S32), the processing of outputting the warning information (S33, S34), and the additional image capturing processing (S35 to S37) are executed. However, only one or two of these types of processing may be executed.

The multiple techniques described as the examples in each of the first to fourth embodiments can be executed in combination. For example, the evaluation information improvement processing described as the example at S31, S32 in the second embodiment (see FIG. 8) may be executed before the ophthalmologic image is input to the mathematical model at S21 of the first embodiment (see FIG. 7). In the above-described embodiments, various types of processing are executed after the evaluation information on the entirety of the ophthalmologic image has been compared with the criterion. However, it may be determined whether or not the evaluation information on a partial region (may be a pixel) of the ophthalmologic image satisfies the criterion. That is, various types of processing may be executed after it has been, for each region of the ophthalmologic image, determined whether or not the evaluation information satisfies the criterion.

Figure 9:
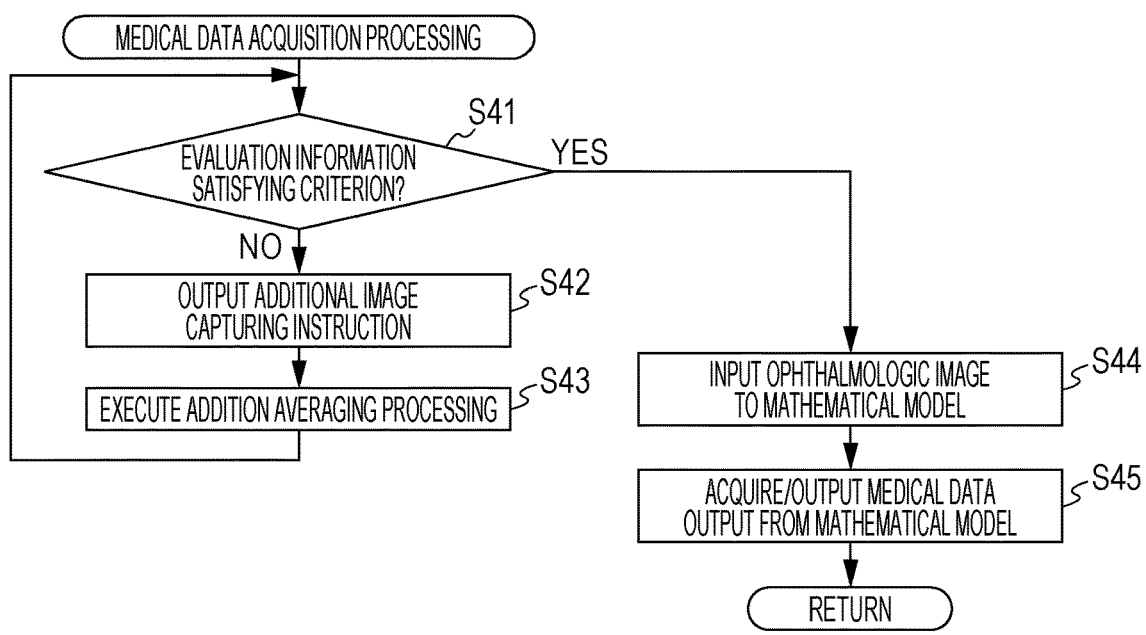
FIG. 9 is a flowchart of medical data acquisition processing executed by an ophthalmologic image processing system 100 of a third embodiment.

Note that the processing of acquiring the ophthalmologic image at S12 of FIG. 6 is one example of an "image acquisition step." The processing of acquiring the evaluation information on the ophthalmologic image at S13 of FIG. 6 is one example of an "evaluation information acquisition step." The medical data acquisition processing shown in FIGS. 7 to 10 is one example of a "medical data acquisition step." The addition averaging processing shown at S41 to S43 of FIG. 9 is one example of an "addition step."

LIST OF REFERENCE SIGNS 11A, 11B Ophthalmologic Image Capturing Apparatus
13A, 13B CPU
14A, 14B Storage Apparatus
21 Ophthalmologic Image Processing Apparatus
23 CPU
24 Storage Apparatus
100 Ophthalmologic Image Processing System

The invention claimed is:

1. An ophthalmologic image processing apparatus for processing an ophthalmologic image as an image of a tissue of a subject eye, the ophthalmologic image processing apparatus comprising a control section configured to execute:
   an image acquisition step of acquiring an ophthalmologic image captured by an ophthalmologic image capturing apparatus,
   an evaluation information acquisition step of acquiring, for the ophthalmologic image acquired at the image acquisition step, evaluation information indicating an appropriateness for acquiring medical data including at least any of an analysis result relating to a disease of the subject eye, an analysis result relating to a structure of the subject eye, and an image converted from the acquired ophthalmologic image, and
   a medical data acquisition step of acquiring the medical data based on the ophthalmologic image acquired at the image acquisition step, wherein
   at the medical data acquisition step, the control section changes a medical data acquisition method according to whether or not the evaluation information acquired at the evaluation information acquisition step satisfies a criterion, at the medical data acquisition step, the control section acquires the medical data in such a manner that the ophthalmologic image is input to a mathematical model trained according to a machine learning algorithm, the mathematical model is trained using multiple training data sets of the ophthalmologic image captured by the ophthalmologic image capturing apparatus as input training data and the medical data corresponding to the input training data as output training data, and the criterion is set based on multiple pieces of the input training data used for training of the mathematical model.

2. The ophthalmologic image processing apparatus according to claim 1, wherein at the medical data acquisition step, the control section acquires the medical data in such a manner that information relating to the evaluation information on the ophthalmologic image is input to the mathematical model together with the ophthalmologic image.

3. The ophthalmologic image processing apparatus according to claim 1, wherein at the medical data acquisition step, the control section executes, for the ophthalmologic image, evaluation information improvement processing of causing the evaluation information on the ophthalmologic image to approach the criterion in a case where the evaluation information on the ophthalmologic image does not satisfy the criterion, and acquires the medical data based on the ophthalmologic image subjected to the evaluation information improvement processing.

4. The ophthalmologic image processing apparatus according to claim 1, wherein at the medical data acquisition step, the control section outputs an instruction for additionally capturing an image of a location identical to that of the ophthalmologic image in a case where the evaluation information on the ophthalmologic image does not satisfy the criterion, and acquires the medical data based on the additionally-captured ophthalmologic image.

5. The ophthalmologic image processing apparatus according to claim 1, wherein at the medical data acquisition step, the control section outputs an instruction for additionally capturing an image of a location identical to that of the ophthalmologic image in a case where the evaluation information on the ophthalmologic image does not satisfy the criterion, and acquires the medical data based on an ophthalmologic image obtained by addition averaging processing of the additionally-captured ophthalmologic image.

6. The ophthalmologic image processing apparatus according to claim 1, wherein the control section acquires multiple ophthalmologic images of the identical tissue of the identical subject eye at the image acquisition step, and acquires the medical data based on at least one, of which evaluation information satisfies the criterion, of the multiple ophthalmologic images.

7. The ophthalmologic image processing apparatus according to claim 1, wherein at the medical data acquisition step, the control section outputs warning information for a user in a case where the evaluation information on the ophthalmologic image does not satisfy the criterion.

8. The ophthalmologic image processing apparatus according to claim 1, wherein at the medical data acquisition step, the control section:

determines whether or not the evaluation information satisfies the criterion for each of multiple partial regions of the ophthalmologic image, and changes the medical data acquisition method for each partial region according to whether or not the evaluation information for that partial region satisfies the criterion.

9. A storage device storing an ophthalmologic image processing program executed by an ophthalmologic image processing apparatus for processing an ophthalmologic image as an image of a tissue of a subject eye, an execution of the ophthalmologic image processing program by a control section of the ophthalmologic image processing apparatus causing the ophthalmologic image processing apparatus to execute:

an image acquisition step of acquiring an ophthalmologic image captured by an ophthalmologic image capturing apparatus, an evaluation information acquisition step of acquiring, for the ophthalmologic image acquired at the image acquisition step, evaluation information indicating an appropriateness for acquiring medical data including at least any of an analysis result relating to a disease of the subject eye, an analysis result relating to a structure of the subject eye, and an image converted from the acquired ophthalmologic image, and a medical data acquisition step of acquiring the medical data based on the ophthalmologic image acquired at the image acquisition step, wherein at the medical data acquisition step, a medical data acquisition method is changed according to whether or not the evaluation information acquired at the evaluation information acquisition step satisfies a criterion, at the medical data acquisition step, the control section acquires the medical data in such a manner that the ophthalmologic image is input to a mathematical model trained according to a machine learning algorithm, the mathematical model is trained using multiple training data sets of the ophthalmologic image captured by the ophthalmologic image capturing apparatus as input training data and the medical data corresponding to the input training data as output training data, and the criterion is set based on multiple pieces of the input training data used for training of the mathematical model.

10. An ophthalmologic image processing system for processing an ophthalmologic image as an image of a tissue of a subject eye, comprising:

an OCT apparatus configured to receive interfering light of reference light and reflected light of measurement light emitted to the tissue of the subject eye to capture an ophthalmologic image as a laminagram image of the tissue, a control section of the ophthalmologic image processing system being configured to execute:

an image acquisition step of acquiring an ophthalmologic image captured by the OCT apparatus, an evaluation information acquisition step of acquiring, for the ophthalmologic image acquired at the image acquisition step, evaluation information indicating an appropriateness for acquiring medical data including at least any of an analysis result relating to a disease of the subject eye, an analysis result relating to a structure of the subject eye, and an image converted from the acquired ophthalmologic image, an addition step of executing, in a case where the evaluation information acquired at the evaluation information acquisition step does not satisfy a criterion, processing of additionally capturing an image of a location identical to that of the ophthalmologic image and addition averaging processing of the image captured in addition to the ophthalmologic image, and a medical data acquisition step of acquiring the medical data in such a manner that the ophthalmologic image subjected to the addition averaging processing is input to a mathematical model trained according to a machine learning algorithm, wherein at the medical data acquisition step, the control section acquires the medical data in such a manner that the ophthalmologic image is input to a mathematical model trained according to a machine learning algorithm, the mathematical model is trained using multiple training data sets of the ophthalmologic image captured by the ophthalmologic image capturing apparatus as input training data and the medical data corresponding to the input training data as output training data, and the criterion is set based on multiple pieces of the input training data used for training of the mathematical model.

* * * * *